(12) United States Patent
Umeda et al.

(10) Patent No.: US 7,047,970 B2
(45) Date of Patent: May 23, 2006

(54) MASK

(75) Inventors: Tomoshige Umeda, Tokyo (JP); Shuji Ishikawa, Tokyo (JP); Toru Yoshihara, Tokyo (JP); Susumu Fujinami, Tokyo (JP); Koji Mimura, Tokyo (JP); Kenichi Ono, Saitama (JP); Tsutomu Mitsuhashi, Saitama (JP)

(73) Assignee: Kao Corporation, Tokyo (JP)

( * ) Notice: Subject to any disclaimer, the term of this patent is extended or adjusted under 35 U.S.C. 154(b) by 837 days.

(21) Appl. No.: 09/783,548

(22) Filed: Feb. 15, 2001

(65) Prior Publication Data

US 2001/0042546 A1 Nov. 22, 2001

(30) Foreign Application Priority Data

Apr. 18, 2000 (JP) ............................. 2000-117047

(51) Int. Cl.
*A62B 18/02* (2006.01)

(52) U.S. Cl. .............................. 128/206.21; 128/203.26

(58) Field of Classification Search ........... 128/206.21, 128/203.26, 204.17
See application file for complete search history.

(56) References Cited

U.S. PATENT DOCUMENTS

| 1,071,109 | A | * | 8/1913 | Stiriz | 128/204.17 |
|---|---|---|---|---|---|
| 3,747,598 | A | * | 7/1973 | Cowans | 128/201.13 |
| 4,829,997 | A | * | 5/1989 | Douwens et al. | 128/201.13 |
| 4,917,119 | A | * | 4/1990 | Potter et al. | 131/273 |
| 5,205,282 | A | * | 4/1993 | Daneshvar | 128/203.26 |
| 5,890,486 | A | * | 4/1999 | Mitra et al. | 128/200.24 |

FOREIGN PATENT DOCUMENTS

| JP | 63-117560 | 7/1988 |
|---|---|---|
| JP | 1-165053 | 11/1989 |
| JP | 5-36442 | 9/1993 |
| JP | 8-231386 | 9/1996 |
| JP | 08/324592 | 12/1996 |
| JP | 9-99084 | 4/1997 |
| JP | 11-342147 | 12/1999 |
| WO | WO 99/51174 | 10/1999 |

OTHER PUBLICATIONS

JIS Japanese Industrial Standard, pp. 1-8, JIS P8117, "Paper and Board-Determination of Air Permeance-Gurley Method", 1998.
JIS Japanese Industrial Standard, pp. 1-5, JIS Z 0208, "Testing Methods for Determination of the Water Vapour Transmission Rate of Moisture—Proof Packaging Materials (Dish Method)", 1976.

* cited by examiner

*Primary Examiner*—Alfred Basichas
(74) *Attorney, Agent, or Firm*—Oblon, Spivak, McClelland, Maier & Neustadt, P.C.

(57) ABSTRACT

A heat generating unit is incorporated in a mask in order to actively supply warm steam, and also drug vapor, to the nose and throat, and moisturize the upper respiratory tract. It is preferable that a metal powder, salt, and water be contained in the heat generating unit, and that an exothermic composition that releases steam in conjunction with the oxidation reaction of the metal powder be used therein. It is preferable that either an inhalation valve or exhalation valve be provided in the main mask body.

12 Claims, 7 Drawing Sheets

X-X Cross-section

X-X Cross-section

X-X Cross-section

X-X Cross-section

X - X Cross-section

MASK

BACKGROUND OF THE INVENTION

1. Field of the Invention

This invention relates to a mask that supplies steam to the nose and throat in order to protect the nose and throat.

2. Description of the Related Art

Since antiquity, the common cold has been a deep-rooted factor in our daily lives. In every era, the common cold has been responsible for the highest proportion of examinations conducted at medical institutions. Common colds begin when viruses in the atmosphere invade, and grow in, such upper respiratory tract region as the nasal membranes and throat. In the dry winter season, in particular, it becomes very easy to catch a cold because, in addition to the fact that immunological resistance declines in the upper respiratory tract, viruses then tend to be dispersed more readily.

Thereupon, masks have conventionally been used as a measure to prevent the common cold by preventing the inhalation of viruses and keeping the throat warm. A type of mask that is made simply by folding gauze and attaching rubber ear loops, and used so as to cover the mouth and nose, is commonly and widely employed. In distinction from such masks, however, Japanese Patent Application Laid-Open No. H9-99084/1997 discloses a mask which more actively protects nose and throat tissue, and has a moist part impregnated with water or an aqueous solution of a perfume or drug. Japanese Utility Model Publication No. H5-36442 discloses a mask containing a moisturizing part comprising a cotton-like synthetic fiber intermixed with a moisture-retaining agent which has been made to sufficiently absorb water.

However, while the conventional masks made simply by folding gauze or the like are effective in retaining heat supplied from body temperature or exhalation, such mask themselves have no heating mechanism, and so are unable to actively supply warm steam to the nose or throat, and are unable to provide moistening to the upper respiratory tract.

Conventional masks which incorporate a moisturizing part or a moist part impregnated with water or drug or the like, while equipped with a supply source for steam or drug vapor, are not provided with a mechanism that promotes the generation of such vapors, so that the generation of steam or drug vapor is only promoted by the inhalation action produced by respiration, and it is very difficult therewith to supply moisture or drugs that effectively prevent colds in the upper respiratory tract.

In WO99/51174, meanwhile, a steam-generating unit is disclosed which uses a steam-generating unit that releases steam by chemical heat generation, to supply steam to the skin of the head, shoulders, neck, face, hips, buttocks, legs, feet, and arms, etc., and to the mucous membranes of the eyes, nose, and throat, etc., thereby providing moisturizing thereto, but no disclosure is made therein concerning combining that steam-generating unit with a mask.

SUMMARY OF THE INVENTION

An object of the present invention is to provide a mask that actively supplies warm steam, and also drug vapor, to the nose and throat, providing moisturizing to the upper respiratory tract.

To attain the object stated above and other objects, the present invention provides a mask comprising a heat generating unit incorporated therein.

In particular, an embodiment is provided wherein a mask comprises a heat generating unit and a main mask body, in which main mask body is provided with an inhalation valve or an exhalation valve, and especially an embodiment wherein the heat generating unit constitutes a steam-generating unit that generates steam.

With the mask of the present invention, because a heat generating unit is incorporated therein, the air inside the mask is warmed, the moisture in the air and the moisture accumulated inside the mask due to exhalation is warmed and supplied to the nose and throat as warm steam, and the upper respiratory tract can be moistened. Accordingly, it is possible to prevent colds, to reduce their symptoms, and to suppress the occurrence of snoring.

In particular, with the mask of the present invention, if an embodiment is adopted wherein a moisture-retaining unit that releases steam is provided separately from the heat generating unit, a sufficient quantity of steam is generated. Accordingly, it becomes possible to definitely supply a sufficient quantity of steam to the upper respiratory tract, and provide moisture to the dry upper respiratory tract, irrespective of whether or not the heat generating unit is capable of generating steam, whereupon the effectiveness in preventing colds and reduction of symptoms can be enhanced.

In the masks of the present invention, with the embodiments thereof wherein the heat generating unit itself releases steam, and particularly with those comprising an exothermic composition containing a metal powder, salt, and water, and releasing steam in conjunction with a metal powder oxidation reaction, steam can be supplied to the upper respiratory tract without providing a moisture-retaining unit separately from the heat generating unit, wherefore cold prevention effectiveness and symptom reduction effectiveness and the like can be enhanced with a simple constitution.

In the mask of the present invention, if according to an embodiment thereof that is provided with a drug carrier unit, or according to an embodiment thereof wherein a drug is dispersed in an exothermic composition, the release of drug vapor from that carrier unit will be promoted by the heat generating unit, wherefore drug vapor will be effectively supplied to the upper respiratory tract together with steam. Accordingly, colds can be prevented and symptoms relaxed more effectively.

In the mask of the present invention, furthermore, if according to an embodiment thereof wherein the main mask body is provided with an inhalation valve or exhalation valve, the breath will be exhausted to the outside without remaining inside the main mask body. With this embodiment, in particular, when the heat generating unit itself is constituted so that it becomes a steam generating unit that releases steam, the steam released from the steam generating unit can be prevented from being exhaled and released to the outside. For that reason, the steam released from the steam generating unit can be effectively inhaled.

With the present invention, furthermore, by steam supplied to the upper respiratory tract is meant, inclusively, both steam produced by the evaporation of water, and the fine water droplets resulting from the condensation of that previously mentioned steam.

DESCRIPTION OF THE PREFERRED EMBODIMENTS

Figure 1A:
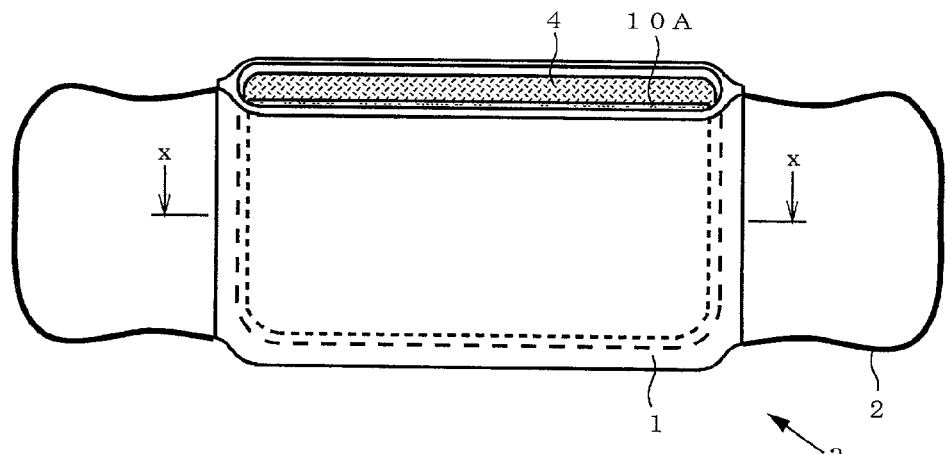
FIGS. 1A and 1B, respectively, are a perspective view of a mask in an embodiment of the present invention, and the x—x section thereof.

A detailed description of the mask of the present invention is now given.

The mask of the present invention is characterized in that a heat generating unit is incorporated therein. By mask, here, is meant something that covers either one or both of the nose and the mouth, and may or may not have a band or bands or the like for securing it to the face.

The heat generating unit may be an electrical heater, a small hot water bottle that uses charcoal or coal or the like, a pocket heater that uses charcoal or benzine or the like, or a composition or the like that generates heat by chemical reaction. In the interest of portability, convenience, and economy, such a composition which generates heat by chemical reaction is preferable.

Heat generation by chemical reaction, here, means heat generated upon a chemical reaction, such as the heat of hydration of calcium chloride, magnesium chloride, calcium oxide, or zeolite or the like, the heat of oxidation of a metal powder, or the heat of neutralization of an acid such as hydrochloric acid and an alkali such as sodium hydroxide. Of these, the use of the heat of oxidation of a metal powder is preferable in the interest of sustaining a prolonged exothermic reaction.

The heat generating unit that utilizes the heat of oxidation of a metal powder is generally what is called a chemical pocket heater. More specifically, such is constituted of an exothermic composition wherein, for example, a powder such as activated carbon or a water adsorbent polymer is made to carry a large quantity of water, to which is added a metal powder such as iron powder, aluminum, zinc, or copper, and a salt such as sodium chloride, potassium chloride, calcium chloride, or magnesium chloride.

For the metal powder in the present invention, iron powder is preferable in the interest of economy. Iron powder produces an exothermic reaction, as expressed in the following formula, and releases water in the system as steam.

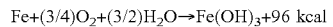

For the iron powder for forming the exothermic composition, specifically, cast iron powder, reduced iron powder, electrolytic iron powder, and scrap iron powder, etc., may be used. Of these, reduced iron powder is preferable. In order to conduct the oxidation reaction in the exothermic composition efficiently, moreover, it is preferable that the iron powder contains 50 wt. % or more of iron powder having a specific surface area of 400 g/m² or greater. The iron powder mixing proportion in the exothermic composition should be 20 to 80 wt. %, and preferably 30 to 60 wt. %.

The exothermic composition can contain various components such as moisture-retaining agents (vermiculite, calcium silicate, silica gel, porous silica-based substances, alumina, pulp, wood powder, water absorbent polymers, etc.) and reaction promoters (activated carbon, carbon black, graphite, etc.).

With a conventional chemical pocket heater, the exothermic composition is contained in a bag comprised of a material exhibiting high air permeability but low moisture permeability, constituted so that the water needed for the reaction does not escape from the heat generating unit.

In the present invention, a heat generating unit where the exothermic composition is contained in a bag comprised of a material of low air permeability but high moisture permeability, as in a conventional chemical pocket heater, may be used. However, when the exothermic composition is contained in a moisture permeable bag, the exothermic composition can be used not only as a heat generating unit, but also as a steam generating composition or steam generating unit, wherefore that is preferable. In that case, the amount of steam released per unit area of the applicable surface of the steam generating unit may preferably be 0.5 mg/cm² or greater. When a heat generating unit having an exothermic composition as contained in a moisture permeable bag is incorporated in a mask, while warming the air sucked into the nose and throat, sufficient steam can be supplied to the air, wherefore this is to be preferred.

The sheet material used for the bag that contains the exothermic composition may preferably exhibit a moisture permeability between about 1000 g/m²·24 h and about 13,000 g/m²·24 h at a temperature of 40° C. and relative humidity of 90%, as provided in JIS Z0208, and a air permeability of 200 seconds/100 cm³ or less, as provided in JIS P8117. More preferable ranges are a moisture permeability of 4000 to 8000 g/m²·24 h and air permeability of 1 to 200 seconds/100 cm³, with 2 to 100 seconds/100 cm³ being even more preferable, and 30 to 70 seconds/10 cm³ being further even more preferable. If the moisture permeability is less than 1000 g/m²·24 h, sufficient steam quantity is not obtained. Conversely, if the moisture permeability exceeds 13,000 g/m²·24 h, there arises a danger of fine particles leaking from the exothermic composition. If the air permeability exceeds 200 seconds/10 cm³, moreover, the speed wherewith the steam released from the exothermic composition passes through the sheet will be slow, whereupon the bag containing the exothermic composition will sometimes swell up and lead to difficulty in actual use. By placing the moisture permeability and air permeability within the ranges noted above, however, the amount of steam released from the heat generating unit surface can be made 0.01 mg/cm²·min or greater, and even 0.5 mg/cm²·min or greater, without causing fine particle leakage or bag swelling.

The amount of steam released here, when, in a room temperature environment (20° C., 65% RH), the heat generating unit is taken out from a container that seals it from the outside air, immediately placed on a pan balance capable of measuring down to 1 mg units, and subjected to a weight measurements for 15 minutes thereafter, is calculated according to formula (1) given below, where $Wt_0$ (g) is the initial measured weight, $Wt_{15}$ (g) the weight 15 minutes later, and S ($cm^2$) the area of that part of the heat generating body surface that is applied to the skin or mucous membrane.

$$\text{Steam release amount (mg/cm}^2\cdot\text{min)}=(Wt_0-Wt_{15})\cdot 1000/15S$$

There is no particular limitation on the base material forming the sheet having the moisture permeability and air permeability noted in the foregoing. That base material may be, for example, a woven fabric, nonwoven fabric, paper, or synthetic paper or the like, having mixed therein one or more types of fiber selected from among such artificial fibers as nylon, vinylon, polyester, rayon, acetate, acrylic, polyethylene, polypropylene, and polyvinyl chloride, or such natural fibers as pulp, cotton, flax, silk, and animal fur, etc. Moreover, gas impermeable films or sheets (such as polyethylene, polypropylene, polyamide, polyester, polyvinyl chloride, polyvinylidene chloride, polyurethane, polystyrene, ethylene vinyl acetate copolymer saponification product, ethylene vinyl acetate copolymer, natural rubber, recycled rubber, and synthetic rubber, etc.), provided with micropores, can also be used. Irrespective of what base material the sheet that is used is made from, by suitably adjusting the size of the sheet micropores, the pore diameter density, and the fabric weight, etc., the moisture permeability and air permeability can be made within the ranges noted earlier.

The bag containing the exothermic composition need only be constituted of a sheet, at least one part whereof has the moisture permeability and air permeability noted earlier; it is not absolutely necessary that the entire surface of the bag be made from a sheet having such moisture permeability and air permeability. In a bag comprising two opposing surfaces, for example, it will be sufficient that one of those surfaces be constituted of a sheet having the moisture permeability and air permeability noted earlier, with the other of those surfaces made of a non-moisture permeable material. Unintended diffusion of the steam released from the exothermic composition can thereby be prevented, and the steam conducted efficiently in the prescribed direction. In cases where the entire surface of the bag is constituted of a sheet having the moisture permeability and air permeability noted above, a non-moisture permeable sheet may be superimposed on one surface of the bag to orient the steam release direction.

When an exothermic composition as described in the foregoing is provided in the mask of the present invention, in an embodiment of the mask for actual use, the mask may be sealed in an air-impermeable outer bag, in the same manner as a commonly known chemical pocket heater, and may be taken out from the outer bag for use, so that the exothermic reaction begins.

In the present invention, there are no particular limitations on the main body shape and base material of the mask into which the heat generating unit is incorporated, so long as the heat generating unit can be loaded therein and the mask covers both the nose and mouth, or either the nose or the mouth.

The shape of the main mask body can be in the form of a bag into and from which the heat generating unit can be freely loaded and unloaded, with elastic bands or the like attached to two opposing sides thereof for looping around the ears to hold the main mask body in place. In that case, there is no particular limitation on the base material of the main mask body so long as heat can be adequately supplied to the nose and mouth, but a material wherewith moisture can be supplied in addition to heat is preferable. In cases where the main mask body is of such type that a chemical pocket heater can be incorporated therein, for example, the base material of the main mask body is made such that at least the material positioned between the chemical pocket heater, on the one hand, and the nose or mouth, on the other, permits a sufficient quantity of steam passage. More specifically, for example, a woven fabric, nonwoven fabric, paper, or synthetic paper, having mixed therein one or more types of fiber selected from among such artificial fibers as nylon, vinylon, polyester, rayon, acetate, acrylic, polyethylene, polypropylene, and polyvinyl chloride, or such natural fibers as pulp, cotton, flax, silk, and animal fur, etc., or a gas impermeable film or sheet such as polyethylene, polypropylene, polyamide, polyester, polyvinyl chloride, polyvinylidene chloride, polyurethane, polystyrene, ethylene vinyl acetate copolymer saponification product, ethylene vinyl acetate copolymer, natural rubber, recycled rubber, and synthetic rubber, etc., provided with through holes, may be used.

For the base material of the main mask body, besides the material comprised of a woven fabric or nonwoven fabric as noted earlier, a plastic molded product exhibiting better shape retention than those can be used.

In terms of the shape of the main mask body, a bag or space for inserting the heat generating unit may be provided in order to facilitate freely loading and unloading the heat generating unit. Thus the main mask body can be used repeatedly, which is advantageous in view of waste disposal problems.

In order to keep the steam reaching the face at a safe temperature, preferably of 50° C. or lower, when the mask is donned, it is preferable that it be suitably provided with a temperature buffering material or space or distance between the heat generating unit and the face, as necessary. The temperature of steam released from the chemical pocket heater noted earlier reaches 60° C. or higher when opened in the atmosphere or in a condition close thereto, without the ventilating air going to the chemical pocket heater being controlled. Therefore, in order to prevent burns, it is preferable that a temperature buffering material or space or dispense be provided between the chemical pocket heater and the face.

As the base material of which the temperature buffer material is constituted, there can be used (1) woven or nonwoven fabric, (2) paper, synthetic paper, or other paper product, (3) porous film or porous sheet formed of plastic, natural rubber, recycled rubber, or synthetic rubber, (4) foam plastics such as urethane foam, provided with through holes, or (5) aluminum or other metal foil provided with through holes. These can be used either singly or in suitable combinations of more than one type. When temperature control is effected using these temperature buffer materials, the temperature buffer material also presents a resistance to the passage of steam, wherefore the material and thickness, etc., of the temperature buffer material should be selected so that the prescribed volume of steam reaches the face.

As to a space or distance provided to control the temperature of steam reaching the face, moreover, it is preferable that the distance from the heat generating unit to the face be made from 1 to 10 cm. If that distance is less than 1 cm, there is a danger of burns being caused, whereas if it exceeds 10 cm, the temperature of the steam reaching the face will be not enough. Such a space or distance can be formed more easily when the main mask body is constituted of a plastic molded material or the like exhibiting better shape retention than a fabric material such as gauze.

In addition, in terms of temperature control modes, there may be proposed a method wherein one surface of the bag containing the exothermic composition is constituted of a moisture permeable sheet, and the other surface of a sheet having fine micropores therein through which oxygen can pass, and a method wherein a poultice layer holding a large volume of water is provided on the outermost surface of the heat generating unit to be applied to the face, and the temperature is controlled by the heat capacity of the water. In the case of the former, it is preferable that the sheet having the fine micropores exhibits an air permeability of 3000 to 40,000 seconds/100 cm$^3$, as provided in JIS P8117. For the poultice layer in the latter case, it is preferable to use a poultice layer comprising an aqueous gel based on a water soluble macromolecular crosslinked by a crosslinking agent.

By suitably changing the quantity of the exothermic composition and/or the particle diameter of the particles constituting the exothermic composition, etc., the reaction speed may be adjusted, whereby the temperature of the steam released from the surface of the heat generating unit can be controlled. The exothermic composition packing density should be 0.05 g to 5 g per cm$^2$, with 0.15 to 2 g per cm$^2$ being preferable. If the packing density is too low, cooling will readily result even though the exothermic composition generates heat, and steam will not be adequately released. If the packing density is too high, conversely, the supply of oxygen to the exothermic composition will become inefficient, and the oxidation reaction will no longer adequately proceed.

When the shape of the bag containing the exothermic composition is a geometric shape such as a sphere or ellipsoid, if the condition wherein such is completely filled with the exothermic composition is taken as a packing ratio of 1, then the packing ratio for the exothermic composition in the bag should be from 0.2 to 0.95, and preferably from 0.3 to 0.8. If the packing ratio is too low, almost no steam will be released, whereas, conversely, if too high, the oxidation reaction will no longer adequately proceed.

In the mask of the present invention, a moisture-retaining unit may be provided that releases steam separately from the heat generating unit. A moisture-retaining unit can be used wherein paper, nonwoven fabric, woven fabric, or a porous polymer or the like is impregnated with water, or a water absorbent polymer is made to absorb water, etc.

In cases where the heat generating unit incorporated in the mask is of a type that does not release steam, such as an exothermic composition in a chemical pocket heater contained in a non-moisture-permeable bag or the like, or an electrical heater or the like, by providing a moisture-retaining unit together with the heat generating unit, it becomes possible to supply sufficient steam to the air inhaled into the nose or throat, and the cold preventing effectiveness of the mask can thereby enhanced, wherefore this is desirable. And, even in cases where the heat generating unit incorporated in the mask is itself capable of generating steam, such as the exothermic composition in a chemical pocket heater contained in a moisture permeable bag or the like, it is preferable to provide a moisture-retaining unit because the volume of steam in the air inhaled into the nose and throat can thereby be further increased.

In the mask of the present invention, furthermore, a drug carrier unit may be deployed. While there is no particular limitation on the type of drug therein, one that soothes inflammations of the respiratory passages, or one that relaxes the nerves or elevates the spirits by a so-called aroma therapy effect is preferable. Also, a drug that is continuously released either by heating or by the supply of steam is preferable.

While there is no particular limitation on the type of such drug, it is desirable that it be a drug whose component is gradually and continuously released by heating or the supply of steam. Specific examples include: such refined oils as angelica oil, peppermint oil, ylang-ylang oil, coriander oil, sandlewood oil, eucalyptus oil, cedarwood oil, jasmine oil, ginger oil, teatree oil, pine oil, nutmeg oil, patchouli oil, bergamot oil, vetiver oil, palmarosa oil, marjoram oil, turpentine oil, rosewood oil, rosemary oil, lavender oil, and Japanese cedar oil; such aromatic components as camphor, geraniol, menthol, citral, citronellol, sionel, α-cedrene, cedrol, terpineol, terpinene, nerol, nerolidol, patchouli alcohol, pinene, phenylethyl alcohol, vetirerol, benzyl acetate, benzyl alcohol, borneol, linalyl acetate, linalool, limonene, and hinokitiol; plant extracts such as aloe extracts, seaweed extracts, chamomile extracts, swertia herb extracts, Japanese angelica root extracts, marronnier extracts, balm mint extracts, hamamelis extracts, eucalyptus extracts, rosemary extracts, and thistle extracts; and such circulation promoters as tocopherol nicotinate, tocopherol acetate, and nicotinamide.

These drugs can be incorporated in the mask by a commonly known method in which drugs are permeated in a carrier unit such as paper or nonwoven fabric or the like and contained such in a bag-shaped mask, or affixed such to the outer surface of the mask.

Alternatively, the drugs noted in the foregoing may be dispersed in an exothermic composition that uses the heat of oxidation of a metal powder. When that is done, the drug component is slowly released also, along with the release of steam from the exothermic composition. The drug component can therefore be prevented from reaching a higher concentration than necessary on the mucous membranes, and can be supplied continuously to the mucous membranes. Hence this is a preferred constitution.

One method for dispersing the drug component in the exothermic composition is, for example, to dissolve that drug in water when it is water soluble, and to disperse it in water when it is water insoluble, and then add that into the exothermic composition. In the latter (water insoluble) case, it is preferable to use a dispersant such as a non-ionic surfactant or the like to facilitate dispersion in water.

The mask in the present invention, meanwhile, comprises a heat generating unit and a main mask body. Included in embodiments thereof, wherein an inhalation valve or exhalation valve is provided in the main mask body, are: (i) one wherein a heat generating unit constituting a heat source is provided, together with, but separately therefrom, a moisture-retaining unit made so that steam is released from the moisture-retaining unit by the heat from the heat generating unit; and (ii) one wherein an exothermic composition such as is used in a chemical pocket heater is used, constituted such that the heat generating unit itself becomes a steam generating unit that releases steam. The present invention can assume the embodiments shown below, for example.

Figure 9A:
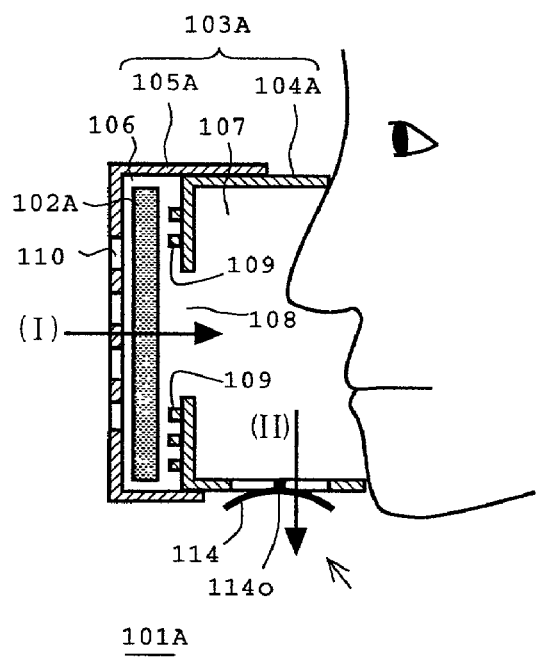
FIGS. 9A, 9B, and 9C, respectively, are a cross section of a mask of the present invention, a front view of the main body thereof, and a front view of a exhalation valve.
Figure 9B:
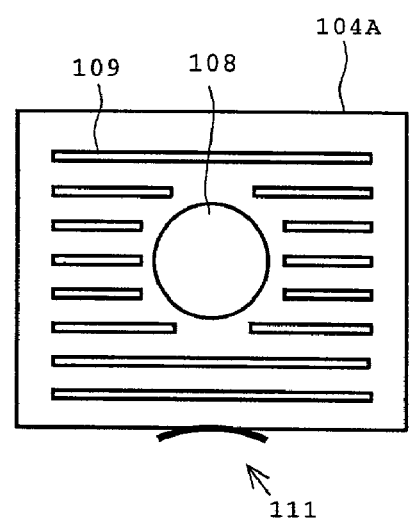
Figure 9C:
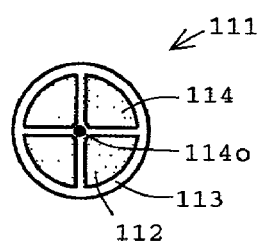

FIG. 9A is a cross section of a mask 101A in one embodiment of the present invention, FIG. 9B is a front view of the main body part 104A thereof, and FIG. 9C is a front view (c) of an exhalation valve 111 used in this mask 101A. This mask 101A comprises a main mask body 103A and a steam generating unit 102A having an exothermic composition contained in a moisture permeable bag.

The main mask body 103A comprises a main body part 104A formed as a molded plastic product exhibiting good shape retention, and a cover 105A. There is no particular limitation on the material of which the main body part 104A or cover 105A is molded, so long as that material exhibits good shape retention. The materials that can be used include such thermoplastic resins as polypropylene, polyethylene, PET, ABS resins, acrylic resins, and vinyl chloride, such thermosetting resins as melamine resins, polyurethane resins, and silicone resins, and such engineering plastics as PBT, polycarbonate, and polyamideimide, etc.

The shape of the main body part 104A is a mask shape that fits tightly to the face as shown. The main body part 104A and cover 105A, in cases where the cover 105A is attached to the main body part 104A, have a space 106 for containing a steam generating unit 102A formed between the main body part 104A and the cover 105A, and are formed so that, when the mask 101A is mounted on the face, a space 107 is formed between the face and the steam generating unit 102A that is contained in the space 106 described above. The steam released from the steam generating unit 102A can be cooled to a suitable temperature by the space 107. An inhalation hole 108 is opened in the center of the main body part 104A, and ribs 109 are provided around the periphery of the inhalation hole 108 in the surface of the main body part 104A, on the steam generating unit 102A side thereof. The ribs 109 prevent the steam generating unit 102A from fitting tightly to the main body part 104A, and enable steam released from the steam generating unit 102A to be efficiently inspired from the breathing hole 108 in the main body part 104A.

In the cover 105A, meanwhile, are provided slits 110 for taking air into the cover 105A. Ribs (not shown) are also provided in the surface of the cover 105A, on the steam generating unit 102A side thereof, as in the main body part 104A.

The main body part 104A and cover 105A can be attached and detached. The parts of these that fit together exhibit a tight fit, and the only openings in the space 106 that contains the steam generating unit 102A are the inhalation hole 108 and the slits 110 in the cover 105A.

An exhalation valve 111 is deployed in the lower part of the main body part 104A. The exhalation valve 111 operates as a so-called check valve which, when the mask 101A is mounted on the face, closes during inhalation and opens during exhalation. The exhalation valve 111 can be constituted as shown in FIG. 9C, for example, such that there are fan-shaped openings 112 in a frame 113, the entire opening 112 is covered by a circular valve member 114, the center $114_0$ of which circular valve member 114 is secured to the frame 113. There is no particular limitation on the material of the circular valve member 114, so long as it is sheet-form material exhibiting pliability. Latex or urethane resins or the like may be used.

When this mask 101A is mounted on the face, during inhalation, air flows in the direction of arrow (I), whereupon sufficient warm steam can be inhaled through the steam generating unit 102A. During exhalation, due to the resistance of the steam generating unit 102A, it is difficult for air to flow toward the steam generating unit 102A, whereupon it flows as indicated by arrow (II), and is quickly expelled to the exterior of the main body part 104A. Accordingly, the loss occurring when steam trapped in the space 106 that contains the steam generating unit 102A is expelled due to exhalation can be reduced.

Figure 10A:
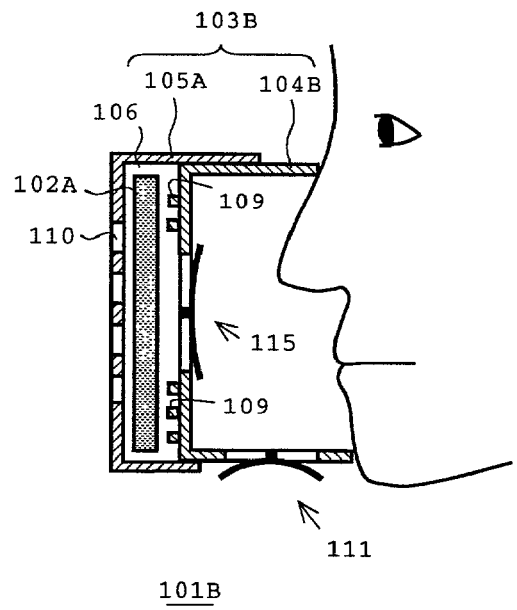
FIGS. 10A and 10B, respectively, are a cross section of a mask of the present invention, and a front view of the main body thereof.
Figure 10B:
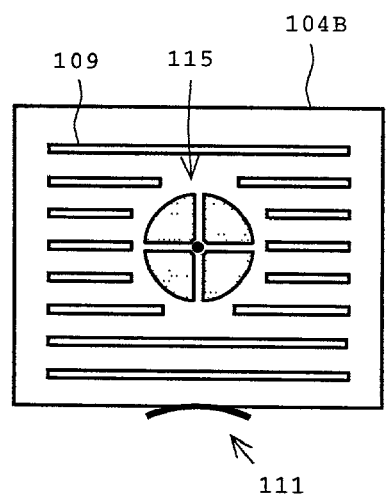

FIG. 10A is a cross section of a mask 101B in another embodiment of the present invention, and FIG. 10B is a front view of the main body part 104B thereof. This mask 101B has an inhalation valve 115 provided in the main body part 104B instead of the inhalation hole 108 in the mask 101A shown in FIGS. 9A to 9C. When the mask 101B is mounted on the face, the inhalation valve 115 opens during inhalation and closes during exhalation. The inhalation valve 115 used may be equivalent to the exhalation valve 111. By providing this inhalation valve 115, exhaled air cannot return to the space 106 containing the steam generating unit 102A, steam can be inspired efficiently through the steam generating unit 102A, and exhaled breath can be expelled to the exterior of the mask 101B.

Figure 11A:
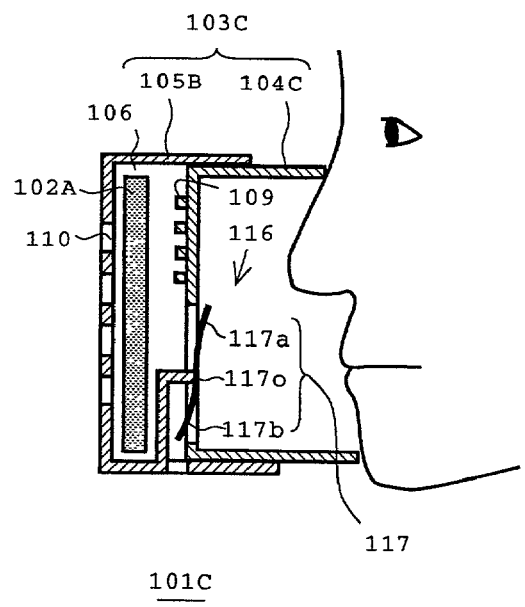
FIGS. 11A and 11B, respectively, are a cross section of a mask of the present invention and a front view of the main body thereof.
Figure 11B:
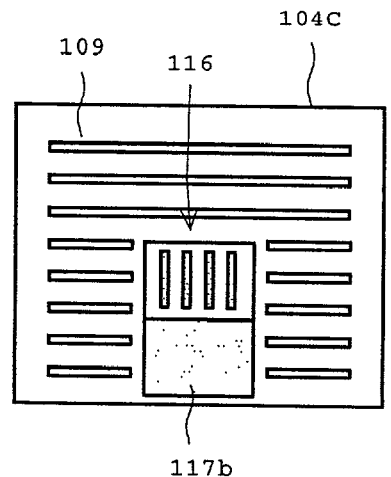

FIG. 11A is a cross section of a mask 101C of still another embodiment of the present, and FIG. 11B is a front view of the main body part 104C thereof. In this mask 10C, an inhalation/exhalation valve 116 is provided in the main body part 104C instead of the inhalation hole 108 and exhalation valve 111 of the mask 101A shown in FIGS. 9A to 9C. This inhalation/exhalation valve 116 directs the flow of air even better during inhalation and exhalation.

The inhalation/exhalation valve 116, to describe it more specifically, is constituted such that the valve member 117 thereof is constituted of a pliable sheet, the center $117_0$ of the valve member 117 is secured to the main body part 104C, the upper part $117_a$ of the valve member 117 opens toward the face so that it acts as an inhalation valve, and the lower part $117_b$ thereof is made so that it opens toward the outside (in the opposite direction from the face) so that it acts as an exhalation valve. With this inhalation/exhalation valve 116, the functions of both an inhalation valve and an exhalation valve can be elicited from a single valve member 117, which is advantageous in that the space for the valve structure can be reduced and lower cost can thereby be effected.

In order to allow exhalation to be exhausted to the outside of the mask 101 when the lower part $117_b$ of the valve member 117 opens toward the outside, in this mask 101C, furthermore, the cover 105B is formed in such shape that it divides the lower part $117_b$ of the valve member 117 and the space 106 containing the steam generating unit 102A, without blocking the lower part $117_b$ of the valve member 117.

Figure 12:
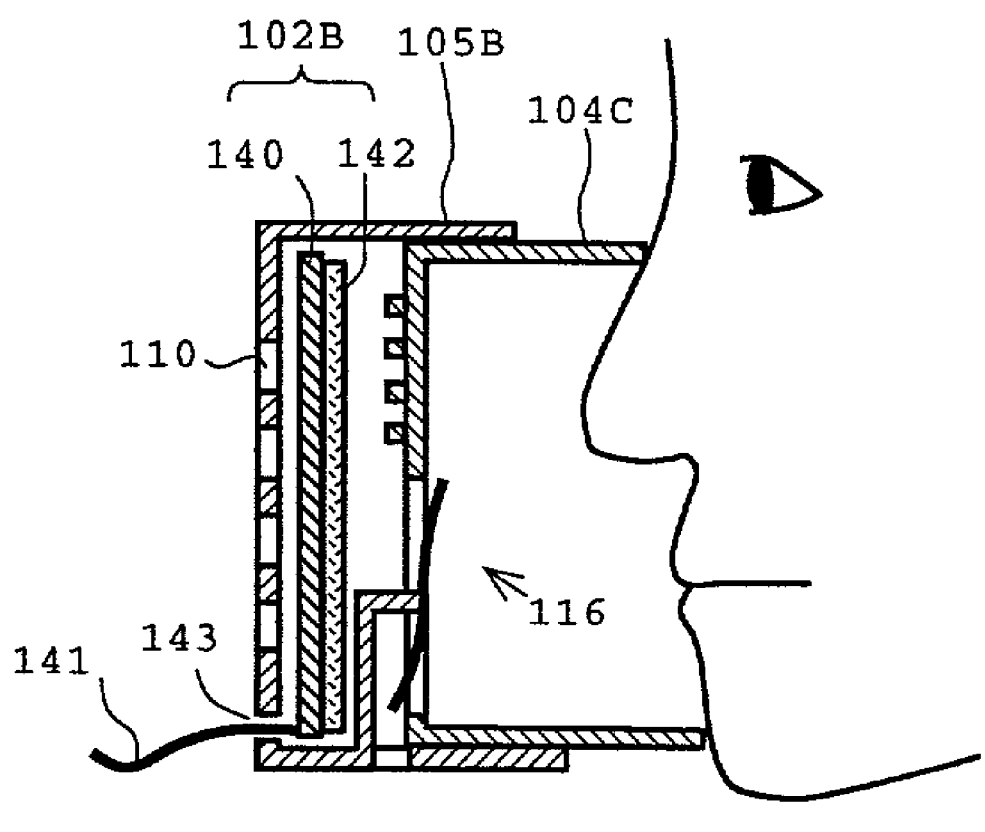
FIG. 12 is a cross section of a mask of the present invention.

The mask 101D in FIG. 12 is constituted such that a steam generating unit 102B comprising an electric heating plate 140 and a moisture-retaining unit 142 are provided instead of the steam generating unit 102A in the mask 101C shown in FIGS. 11A and 11B which uses an exothermic composition, with a hole 143 for passing a cord 141 for the electric heating plate 140 opened in the cover 105B.

For the moisture-retaining unit 142, use may be made of paper, nonwoven fabric, woven fabric, or a porous polymer or the like impregnated with water, or a water absorbent polymer in which water has been absorbed.

The mask of the present invention can be made in various embodiments other than the embodiments shown in the drawings. In the mask 101B shown in FIGS. 10A and 10B, for example, only an inhalation valve 115 may be provided in the main body part 104B, without providing an exhalation valve 111. Even when that is the case, the flow of air during inhalation can be better directed, and warm steam inhaled more efficiently, than in a conventional mask not provided with either an inhalation valve or an exhalation valve.

The material from which the main mask body is molded is not particularly limited so long as it can hold the steam generating unit and is provided with an inhalation valve or an exhalation valve. Accordingly, in the mask 101A shown in FIGS. 9A to 9C, for example, a bag-shaped member made of a pliable material such as woven fabric, nonwoven fabric, paper, synthetic paper, or film, etc., may be used instead of the molded plastic product that exhibits good shape retention. When, moreover, for the material of which the main body part 104A and cover 105A is molded, a sheet material is used which exhibits a moisture permeability of 600 g/m²·24 h or more, according to the ASTM method (E-96-80D method), but preferably of 1000 g/m²·24 h or more, and more preferably of 1500 to 3200 g/m²·24 h, it is not then absolutely necessary either to provide the inhalation hole 108 in the main body part 104A or to provide the slits 110 in the cover 105A. Furthermore, in embodiments of the present invention wherein an inhalation valve or exhalation valve is provided, as in the embodiments of the mask described in the foregoing wherein no inhalation valve or exhalation valve is provided, when necessary, a carrier of paper or nonwoven fabric or the like can be permeated with a drug to form a drug carrier unit, and that carrier unit incorporated into the mask 101A by a commonly known method, such as that of containing it in the open space in the main mask body 103 in the mask 101A shown in FIGS. 9A to 9C, or affixing it to the face-side surface of the main body part 104A of the main mask body 103A, for example. A drug component may also be dispersed in the exothermic composition.

For the steam generating unit, moreover, when an exothermic composition that uses the heat of oxidation of a metal powder is used, as shown in FIGS. 9A, 9B, and 9C to FIGS. 11A and 11B, a moisture-retaining body that releases steam may be incorporated in the main mask body, separately from the steam generator. When that is done, an advantage is realized in that the amount of steam in the air taken into the nose and throat can then be increased.

The rubber ear loops or securing bands or the like provided in conventional mask may be provided as necessary to the main mask body so that the mask can easily be maintained in a condition wherein it is mounted to the face.

Embodiments of the present invention are now described specifically while referencing the drawings. In the drawings, the same symbols indicate the same or equivalent configuring elements.

EXAMPLES

Example 1

Figure 1B:
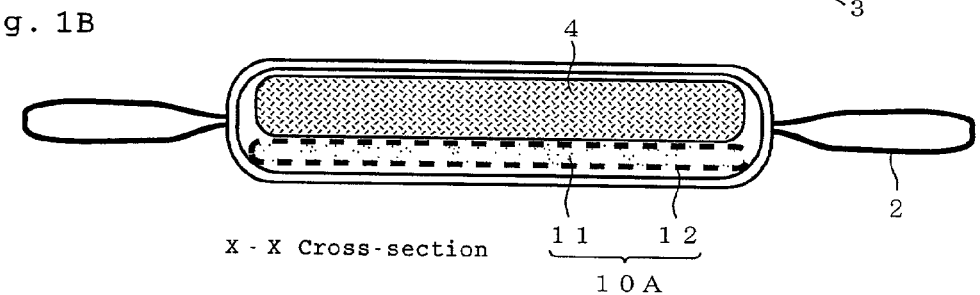

A main mask body 3 (13 cm on the long side, 8 cm on the short side) comprising a bag 1 and rubber ear loops 2 as shown in FIGS. 1A and 1B was fabricated. The bag 1 in this case was formed from cotton.

Separately, an exothermic composition 11 having the composition indicated in Table 1 was prepared, 20 g of this exothermic composition 11 were placed in a moisture permeable heat generating unit inner bag 12 made of a polypropylene fiber nonwoven fabric to form a heat generating unit 10A, and that was contained inside the bag 1 of the main mask body 3 as shown in FIGS. 1A and 1B.

For a temperature buffer material 4, a polypropylene fiber nonwoven fabric (15 mm in thickness) was prepared, and this was contained inside the bag 1 of the main mask body 3 as shown in FIG. 1 to make the mask of this embodiment.

TABLE 1

| Exothermic composition | Wt. % |
|---|---|
| Activated carbon | 20 |
| Sodium chloride | 5 |
| Iron powder | 50 |
| Water | 25 |

Example 2

Figure 2A:
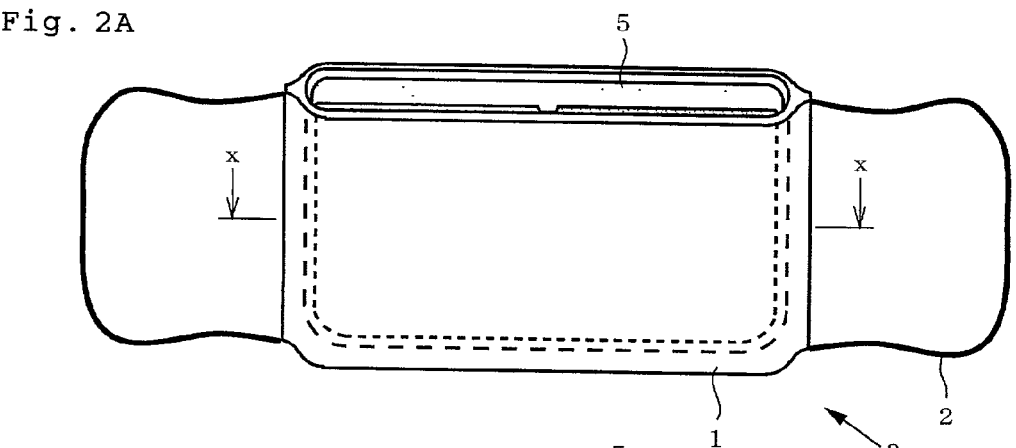
FIGS. 2A and 2B, respectively, are a perspective view of a mask in an embodiment of the present invention, and the x—x section thereof.
Figure 2B:
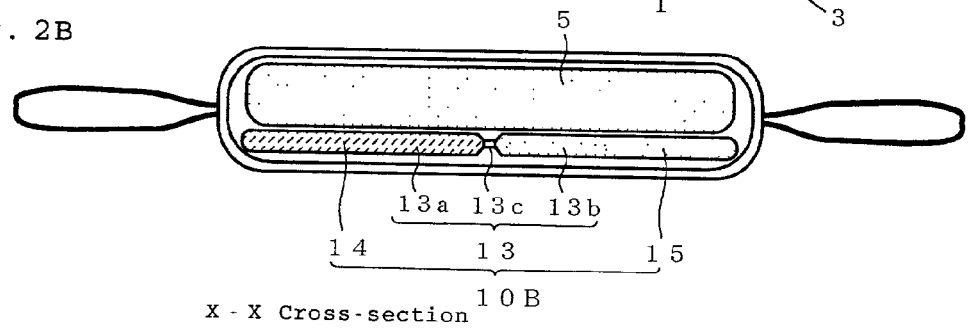

Using a sheet comprised of a water-impermeable polyethylene, a heat generating unit inner bag 13 was fabricated having the interior thereof divided into two containing sections 13a and 13b, as shown in FIG. 2B, such that, by inserting contents into those containing sections 13a and 13b and pressing on them, the two containing sections 13a and 13b are easily interconnected at the boundary 13c therebetween. Into one of the containing sections, 13a, were placed 7 g of calcium chloride 14, and in the other containing section, 13b, were placed 30 g of water 15 to constitute a heat generating unit 10B. This heat generating unit 10B was contained inside the bag 1 of the main mask body 3 as in Example 1.

A high-density nonwoven fabric was impregnated with water and contained in an inner bag made of a nonwoven fabric comprised of a moisture permeable and water-impermeable polypropylene fiber to fabricate a moisture-retaining unit 5, and that was contained inside the bag 1 of the main mask body 3 to make the mask of Example 2.

Example 3

Figure 3A:
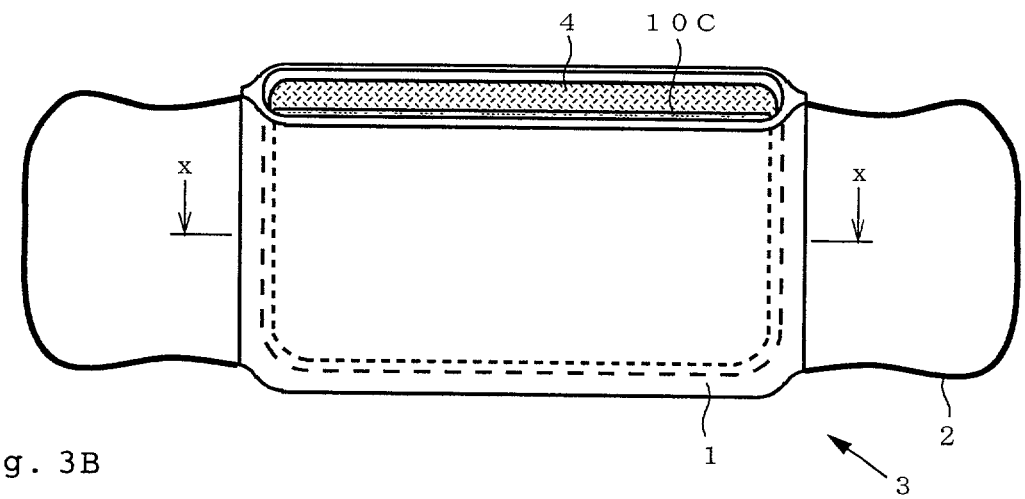
FIGS. 3A and 3B, respectively, are a perspective view of a mask in an embodiment of the present invention, and the x—x section thereof.
Figure 3B:
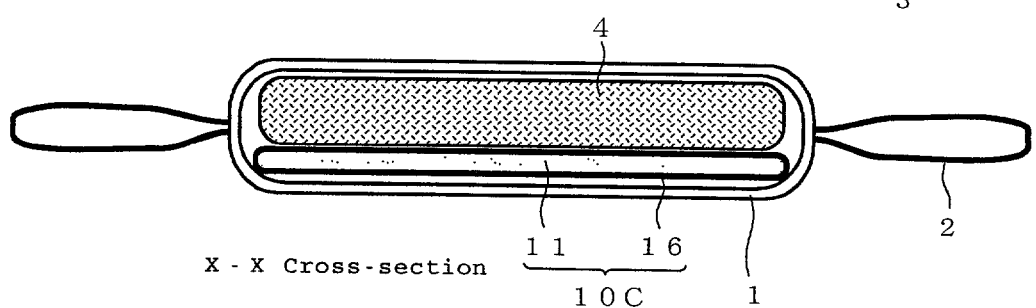

As shown in FIGS. 3A and 3B, an exothermic composition 11 like that in Example 1 was contained in an air permeable and non-moisture permeable heat generating body inner bag 16 that passes oxygen but does not pass steam to fabricate a heat generating body 10C not having a steam generating capability. Thus the mask of this embodiment was fabricated in the same way as in Example 1, except for using the heat generating unit 10C instead of the heat generating unit 10A.

Example 4

Figure 4A:
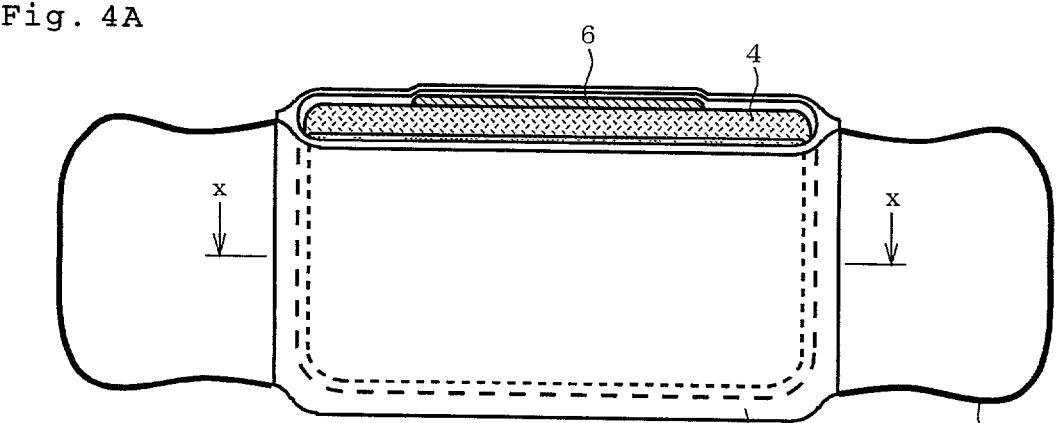
FIGS. 4A and 4B, respectively, are a perspective view of a mask in an embodiment of the present invention, and the x—x section thereof.
Figure 4B:
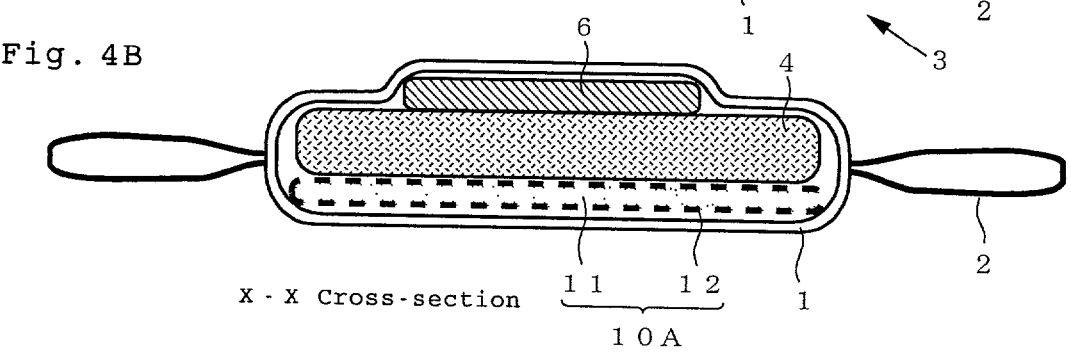

A drug carrier unit 6 carrying menthol, eucalyptus oil, and turpentine oil in filter paper was fabricated, and this was loaded into the bag 1 of the main mask body 3 of the mask of Example 1, as shown in FIGS. 4A and 4B, to fabricate the mask of this Example.

Example 5

The mask of this example was fabricated in the same way as in Example 4 except in that the drug carrier unit 6 of Example 4 was loaded in the mask of Example 3.

Example 6

Figure 5A:
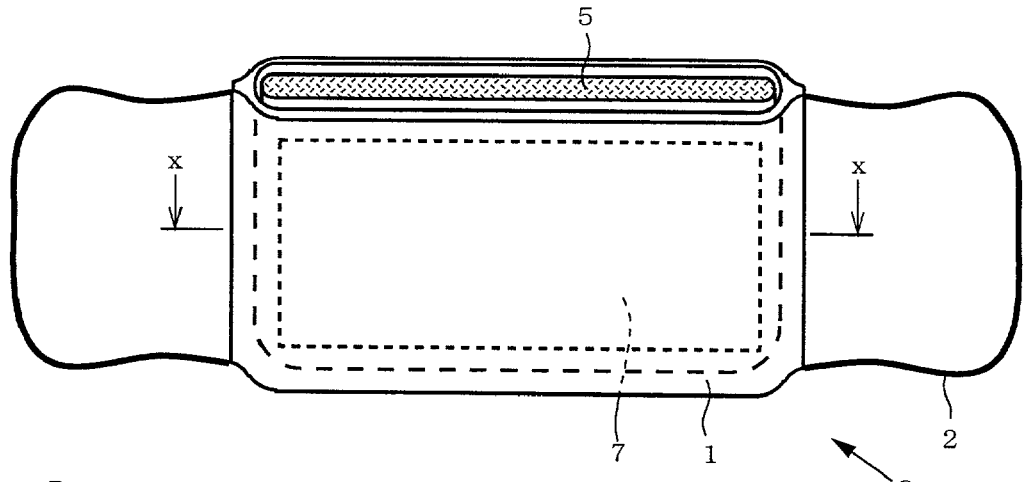
FIGS. 5A and 5B, respectively, are a perspective view of a mask in an embodiment of the present, and the x—x section thereof.
Figure 5B:
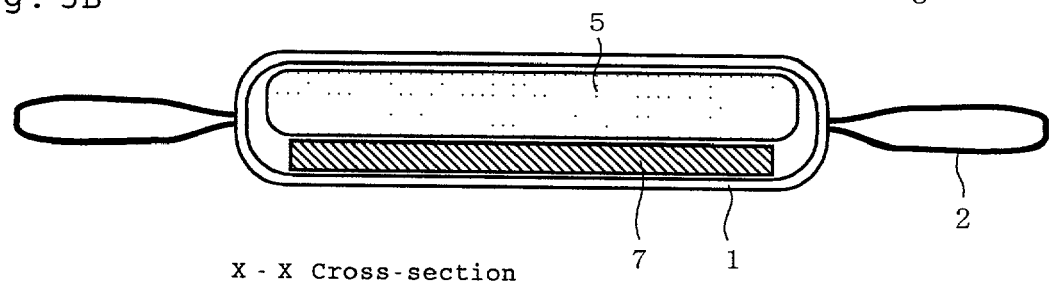

As shown in FIG. 5, a commercially available pocket heater 7 (Hakukin Kairo, made by Hakukin K.K.) of a type wherein benzine is burned in the presence of a platinum catalyst was used instead of the heat generating unit 10B of Example 2 to fabricate the mask of this Example.

Example 7

The mask of this example was fabricated in the same way as in Example 6 except in that the drug carrier unit 6 of Example 4 was loaded in the mask of Example 6.

Example 8

Figure 6:
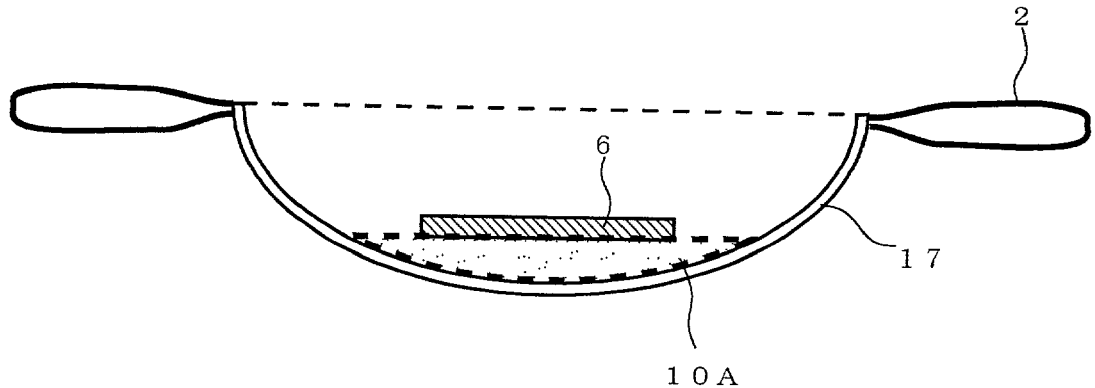
FIG. 6 is a cross section of a mask in an embodiment of the present invention.

As shown in FIG. 6, a main mask body comprising a molded mask product 17 made of polypropylene having a semispherical cross-section and rubber ear loops 2 attached to each end thereof was fabricated. The heat generating unit 10A of Example 1 was secured to the inner surface of this molded mask product 17, and onto that was secured the drug carrier unit 6 of Example 4 to fabricate the mask of this Example. This mask, when donned, exhibited a distance of approximately 3 cm between the face and the heat generating unit.

Example 9

Figure 7:
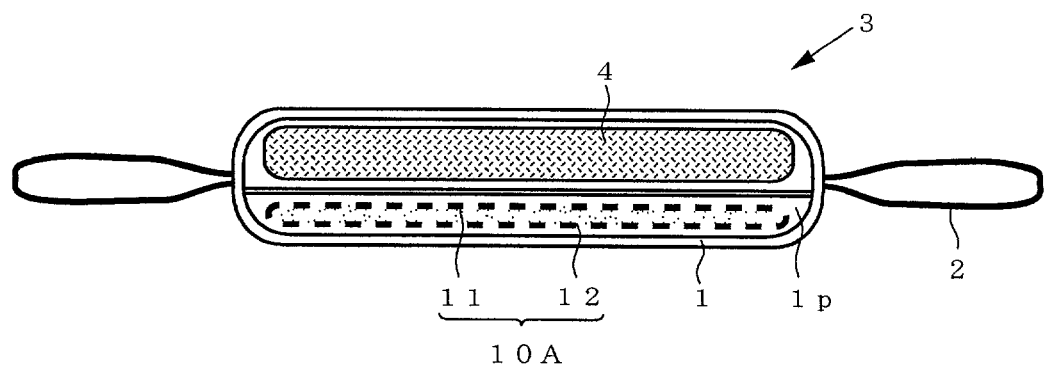
FIG. 7 is a cross section of a mask in an embodiment of the present invention.

The mask of this example was fabricated in the same way as Example 1 except in that, as shown in FIG. 7, a pocket 1p capable of containing the heat generating unit 10A so as to be freely attachable and detachable was provided in the bag 1, and the heat generating unit 10A was inserted into that pocket 1p.

With this example, the heat generating unit 10A can be taken out from the pocket 1p and thrown away after use, and the main mask body 3 can be reused after inserting a new heat generating unit into the pocket 1p.

Example 10

Figure 8:
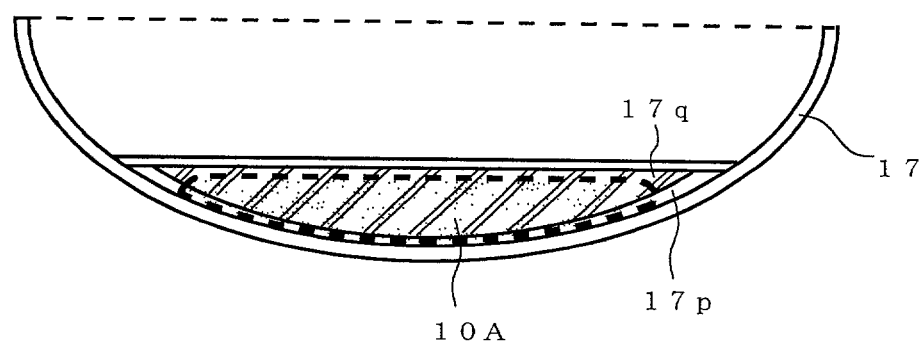
FIG. 8 is a cross section of a mask in an embodiment of the present invention.

As shouwn in FIG. 8, a main mask body comprising a molded mask product 17 made of polypropylene having a semispherical cross-section was fabricated. The mask of this Example was fabricated by forming an empty section 17p equipped with a cover 17q, as a pocket wherein the heat generating unit 10A of Example 1 can be inserted so as to be freely attachable and detachable, on the inner surface of the molded mask product 17, and inserting the heat generating unit 10A into that empty section 17p.

To use this mask, the main mask body is held in the hand and applied to the mouth or nose. The heat generating unit 10A can be taken out from the empty section 17p and thrown away after use, and the main mask body can be reused after inserting a new heat generating unit into the empty section 17p.

Comparative Example 1

A mask was fabricated in the same way as in Example 1 except in that the heat generating unit 10A was not used.

Comparative Example 2

A mask was fabricated in the same way as in Example 2 except in that the heat generating unit 10A was not used.

Evaluation

The masks fabricated in each of the Examples and comparative examples were used for 30 minutes by 10 monitors (1 to 10) exhibiting cold symptoms, and evaluations were made, according to the criteria noted below, on effectiveness in relieving (i) throat soreness, (ii) nasal secretion, and (iii) nasal congestion. The results obtained are shown in Table 2.

(Evaluation Criteria)

(i) Throat Soreness

Rank Criteria

AA: Throat soreness was completely relieved.
A: Throat soreness was considerably relieved.
B: Throat soreness was slightly relieved.
C: Throat soreness was not relieved.

(ii) Nasal Secretion

Rank Criteria

AA: Nasal secretion was completely relieved.
A: Nasal secretion was considerably relieved.
B: Nasal secretion was slightly relieved.
C: Nasal secretion was not relieved.

(iii) Nasal Congestion

Rank Criteria

AA: Nasal congestion was completely relieved.
A: Nasal congestion was considerably relieved.
B: Nasal congestion was slightly relieved.
C: Nasal congestion was not relieved.

TABLE 2

| Example | | Monitor | | | | | | | | | |
|---|---|---|---|---|---|---|---|---|---|---|---|
| | | 1 | 2 | 3 | 4 | 5 | 6 | 7 | 8 | 9 | 10 |
| 1 | Throat soreness | AA | AA | AA | AA | AA | AA | AA | AA | AA | AA |
| | Nasal Secretion | AA | AA | AA | AA | AA | AA | AA | AA | A | AA |
| | Nasal Congestion | A | A | AA | AA | AA | AA | AA | A | A | AA |
| 2 | Throat soreness | AA | AA | AA | AA | AA | AA | AA | AA | AA | AA |
| | Nasal Secretion | AA | AA | AA | AA | AA | AA | AA | AA | A | AA |
| | Nasal Congestion | A | A | AA | AA | AA | AA | AA | A | A | AA |
| 3 | Throat soreness | B | AA | AA | B | AA | A | AA | B | B | AA |
| | Nasal Secretion | B | A | AA | A | AA | AA | AA | A | B | AA |
| | Nasal Congestion | B | B | AA | B | AA | AA | AA | B | B | AA |
| 4 | Throat soreness | AA | AA | AA | AA | AA | AA | AA | AA | AA | AA |
| | Nasal Secretion | AA | AA | AA | AA | AA | AA | AA | AA | AA | AA |
| | Nasal Congestion | AA | AA | AA | AA | AA | AA | AA | AA | AA | AA |
| 5 | Throat soreness | AA | AA | AA | A | AA | A | AA | A | A | AA |
| | Nasal Secretion | AA | A | AA | A | AA | AA | AA | A | B | AA |
| | Nasal Congestion | AA | B | AA | A | AA | AA | AA | B | A | AA |
| 6 | Throat soreness | AA | AA | AA | AA | AA | A | AA | AA | AA | AA |
| | Nasal Secretion | AA | AA | AA | AA | AA | AA | AA | AA | A | AA |
| | Nasal Congestion | AA | A | AA | A | AA | AA | AA | A | A | A |
| 7 | Throat soreness | AA | AA | AA | AA | AA | AA | AA | AA | AA | AA |
| | Nasal Secretion | AA | AA | AA | AA | AA | AA | AA | AA | AA | AA |
| | Nasal Congestion | AA | AA | AA | AA | AA | AA | AA | AA | AA | AA |
| 8 | Throat soreness | AA | AA | AA | AA | AA | AA | AA | AA | AA | AA |
| | Nasal Secretion | AA | AA | AA | AA | AA | AA | AA | AA | AA | AA |
| | Nasal Congestion | AA | AA | AA | AA | AA | AA | AA | AA | AA | AA |
| Comparative Example | | | | | | | | | | | |
| 1 | Throat soreness | C | C | C | C | C | C | C | C | C | C |
| | Nasal Secretion | C | C | C | C | C | C | C | C | C | C |
| | Nasal Congestion | C | C | C | C | C | C | C | C | C | C |
| 2 | Throat soreness | C | C | A | C | C | B | B | B | C | C |
| | Nasal Secretion | C | C | C | C | C | C | C | C | C | C |
| | Nasal Congestion | C | C | B | C | C | C | C | C | C | C |

As is apparent from Table 2, the Examples of the present invention, as compared with the comparative examples wherein no heat generating unit was used, all exhibited high effectiveness in relieving cold symptoms. Examples 1, 2, 4, 6, 7, and 8, in particular, wherein steam is actively released from the mask, exhibited high effectiveness in relieving cold symptoms as compared to Examples 3 and 5 having themselves no steam generating capability. Examples 4, 7, and 8, wherein a drug carrier unit was used, exhibited even more outstanding relief effectiveness.

Example 11

The mask 101A in the Example shown in FIGS. 9A to 9C was fabricated as follows.

First, as indicated in Table 3, a water absorbent polymer (product name: Aqualic CA, made by Nippon Shokubai Kagaku Kogyo Co., Ltd.), vermiculite (made by Shinsei Micron), and activated carbon (product name: Carbolafin, made by Takeda Chemical Industries, Ltd.) were mixed. Into this powder mixture was mixed a liquid mixture wherein lavender oil and 5 wt. % salt water were dispersed in a nonionic surfactant (product name: Softanol, made by Nippon Shokubai Kagaku Kogyo Co., Ltd.). Iron powder (product name: RKH, made by Dowa Teppun Kogyo) was next mixed in, and an exothermic composition was obtained. The steam generating unit 102A was then fabricated by placing that exothermic composition in a moisture permeable bag (base material: melt-blown polypropylene nonwoven fabric; size: 90×74 mm).

The main body part 104A of the main mask body 103A was fabricated by deploying a valve member 14 made of natural rubber in the bottom surface of a molded plastic product (size: 85×75 mm) having an inhalation hole 8 of diameter 27 mm in one surface thereof. The cover 105A was fabricated from a similar molded polypropylene product made to fit the main body part 104A.

The steam generating unit 102A described above was contained in the space 6 between the cover 105A and main body part 104A of this main mask body 103A to make the mask 101A.

TABLE 3

|  | (Unit: wt. %) |
|---|---|
| Water absorbent polymer | 5 |
| Activated carbon | 4 |
| Vermiculite | 4 |
| 5 wt. % BaCl solution | 36 |
| Lavender oil | 0.4 |
| Nonionic surfactant | 0.4 |
| Iron powder | 50.2 |

Example 12

The mask 101B of the Example shown in FIGS. 10A and 10B was fabricated.

In this case, the steam generating unit 102A was fabricated in the same way as in Example 11. The main mask body 103B was fabricated by deploying an inhalation valve 115 having a valve member made of natural rubber at the position of the inhalation hole 108 in the main body part 104A in Example 11. The steam generating unit 102A was contained in the space 106 between the cover 105A and main body part 104B of the main mask body 103B to make the mask

Example 13

The mask 101C of the Example shown and 11B was fabricated.

In this case, the steam generating unit 102A was fabricated by using eucalyptus oil instead of lavender oil when preparing the exothermic composition of Example 11.

The main mask body 103C was fabricated by deploying, instead of the inhalation hole 108 and exhalation valve 111 in the main body part 104A in Example 1, a combination inhalation/exhalation valve 116 having a valve body 117 made of natural rubber in the center 117$_0$ thereof, secured to the main body part 104C. The steam generating unit 102A described above was contained in the space 6 between the cover 105B and main body part 104C of this main mask body 103C to make the mask 101C.

Example 14

In this case, the electrical heating plate 140 used was of a size of 80×80×10 mm and weight of 50 g, generating 300 W of heat. The moisture-retaining body 142 used was made by placing 1 g of a water absorbent polymer (product name: Aqualic CA, made by Nippon Shokubai Kagaku Kogyo Co., Ltd.) caused to retain 5 g of water into a moisture permeable bag (base material: melt-blown polypropylene nonwoven cloth; size: 80×80 mm).

Comparative Example 3

A commercially available gauze mask was provided.

Evaluation

Functional tests were conducted with 10 monitors using Examples 11 to 14 and Comparative Example 3. Evaluations were obtained from the monitors according to the following criteria. The results are given in Table 4.

Evaluation Criteria
Rank Criteria
A: Sufficient inhalation of steam could be sensed.
B: inhalation of steam could be sensed, but inhalation volume was felt to be inadequate.
C: Almost no steam inhalation could be sensed.

TABLE 4

|  | Monitor | | | | | | | | | |
|---|---|---|---|---|---|---|---|---|---|---|
|  | 1 | 2 | 3 | 4 | 5 | 6 | 7 | 8 | 9 | 10 |
| Example | | | | | | | | | | |
| 11 | A | A | A | A | A | A | A | A | A | A |
| 12 | A | A | A | A | A | A | A | A | A | A |
| 13 | A | A | A | A | A | A | A | A | A | A |
| 14 | A | A | A | A | A | A | A | A | A | A |
| Comparative Example | | | | | | | | | | |
| 3 | C | C | B | C | C | C | C | C | C | C. |

It will be understood from the results given in Table 4 that steam inhalation can be sensed with the masks in the Examples having either an inhalation valve or exhalation valve in the main body part, and that almost no steam inhalation can be sensed with a commercially sold gauze mask having neither inhalation valve nor exhalation valve, due to the fact that only the moisture contained in the exhaled breath is the supply source for steam.

Example 15

An exothermic composition having the composition given in Table 3 was prepared as in Example 11.

Also, a bag measuring 8×8 cm was fabricated, using a sheet exhibiting a moisture permeability of 8200 g/m$^2$·24 h (40° C., 90% relative humidity) and an air permeability of 25 seconds/100 cm$^3$. In this bag was contained 25 g of the exothermic composition noted above to fabricate the steam generating unit 102A, which was sealed in an airtight bag.

Separately, the mask 101C in the Example shown in FIGS. 11A and 11B was fabricated as in Example 13.

The steam generating unit 102A filled with the exothermic composition described above was taken from the airtight bag. The steam generating unit 102A described above was then immediately contained in the space 6 between the cover 105B and main body part 104C of the main mask body 103C to make the mask 101C.

This steam generating unit 102A, 60 seconds after its removal from the airtight bag, released steam at a temperature of 40 to 45° C. for 10 minutes. During that time, there was no swelling in the bag containing the exothermic composition. No adhering powder was found on the surface of the bag 2 after steam release was finished.

What is claimed is:

1. A mask, comprising a heat generating unit incorporated therein, wherein said heat generating unit is configured to generate heat by chemical reaction, wherein said heat generating unit comprises an exothermic composition containing a metal powder, salt, and water, which heat generating unit releases steam in conjunction with oxidation reaction of said metal powder, thereby generating a therapeutic vapor of inhalation.

2. The mask according to claim 1, having a moisture-retaining unit, separate from said heat generating unit.

3. The mask according to claim 1, wherein said heat generating unit is configured to be attached and detached.

4. The mask according to claim 1, further comprising a temperature buffering between said heat generating unit and a face when said mask is donned.

5. The mask according to claim 1, further having a drug carrier unit.

6. The mask according to claim 1, wherein said heat generating unit comprises an exothermic composition with a drug dispersed in said exothermic composition.

7. The mask according to claim 1, further comprising a bag containing the exothermic composition, which bag has a surface adapted to be applied to a face, and which bag comprises a moisture permeable sheet exhibiting a moisture permeability between about 1000 $g/m^2 \cdot 24$ h and about 13,000 $g/m^2 \cdot 24$ h under conditions of a temperature of 40° C. and relative humidity of 90%, and an air permeability of 200 seconds/100 $cm^3$ or less.

8. The mask according to claim 1, configured to have a space and distance between said heat generating unit and a face when said mask is donned.

9. The mask according to any one of claims 1–2, 6–10, wherein main mask body is provided with at least one of an inhalation valve and an exhalation valve.

10. The mask according to claim 9, wherein an inhalation valve and an exhalation valve are provided separately in said main mask body.

11. The mask according to claim 9, wherein an inhalation/exhalation valve is provided in said main mask body.

12. A mask comprising:
a main mask body; and
heat generating means for generating steam in said main mask body by an exothermic oxidation chemical reaction,
wherein said steam generates a therapeutic vapor for inhalation.

* * * * *